United States Patent [19]

DeWall

[11] 3,946,735

[45] Mar. 30, 1976

[54] MEDICAL DRAINAGE DEVICE

[76] Inventor: Richard A. DeWall, 421 Thornhill Road, Dayton, Ohio 45419

[22] Filed: May 13, 1974

[21] Appl. No.: 469,423

[52] U.S. Cl............................. 128/278; 128/350 V
[51] Int. Cl.²......................................... A61M 1/00
[58] Field of Search ....... 128/276, 277, 230, 350 V, 128/278, 231, 297; 222/210, 213; 417/472; 141/25

[56] References Cited
UNITED STATES PATENTS

| | | | |
|---|---|---|---|
| 3,111,125 | 11/1963 | Schulte | 128/350 V |
| 3,417,750 | 12/1968 | Carson | 128/278 |
| 3,421,504 | 1/1969 | Gibbons | 128/278 |
| 3,595,240 | 7/1971 | Mishler | 128/350 V |
| 3,683,913 | 8/1972 | Kurtz et al. | 128/276 |

Primary Examiner—Robert W. Michell
Assistant Examiner—Henry S. Layton
Attorney, Agent, or Firm—Wegner, Stellman, McCord, Wiles & Wood

[57] ABSTRACT

A surgical suction system which may be driven in a plurality of different ways. The basic component of the system is an enlarged container having an inlet and an outlet and being formed of a resilient material of the type which restores itself to its original shape following distortion from the original shape. The inlet is connected to apparatus for insertion to an area of a patient to be drained and includes a check valve for allowing fluid to pass into the container through the inlet while precluding substantial backflow. The outlet may be connected to a check valve and/or a regulated vacuum source. The walls of the container include pleated formations so that the same may be compressed to reduce the volume to establish a vacuum therein.

10 Claims, 4 Drawing Figures

U.S. Patent  March 30, 1976  3,946,735
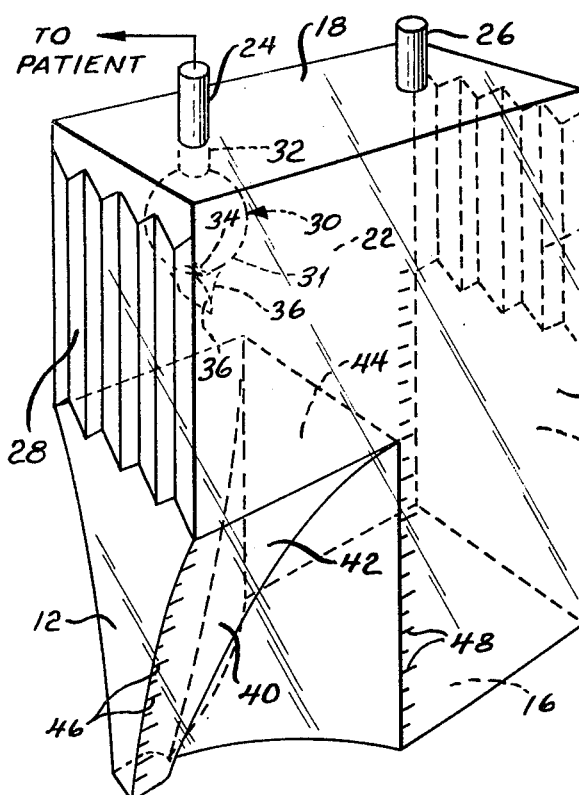
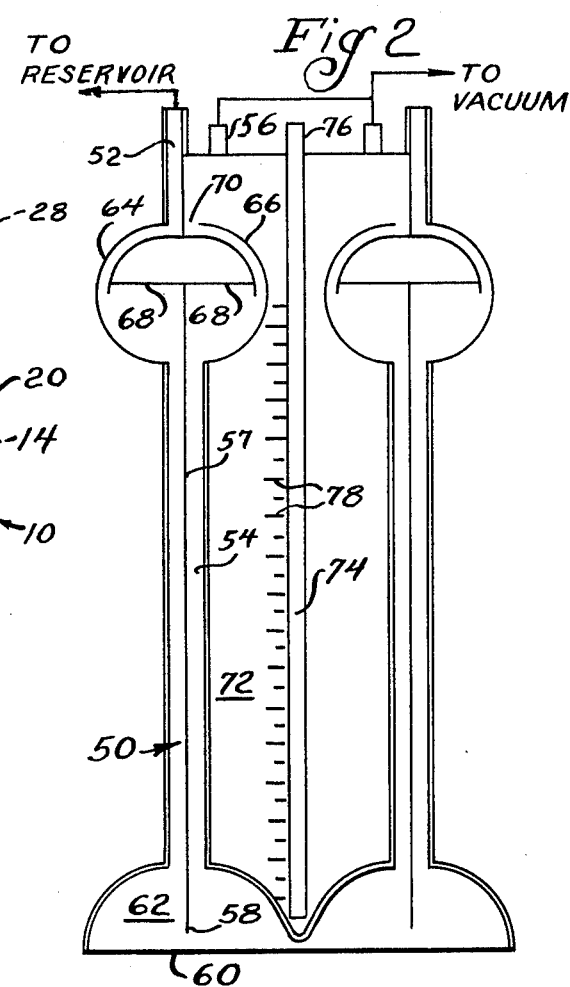
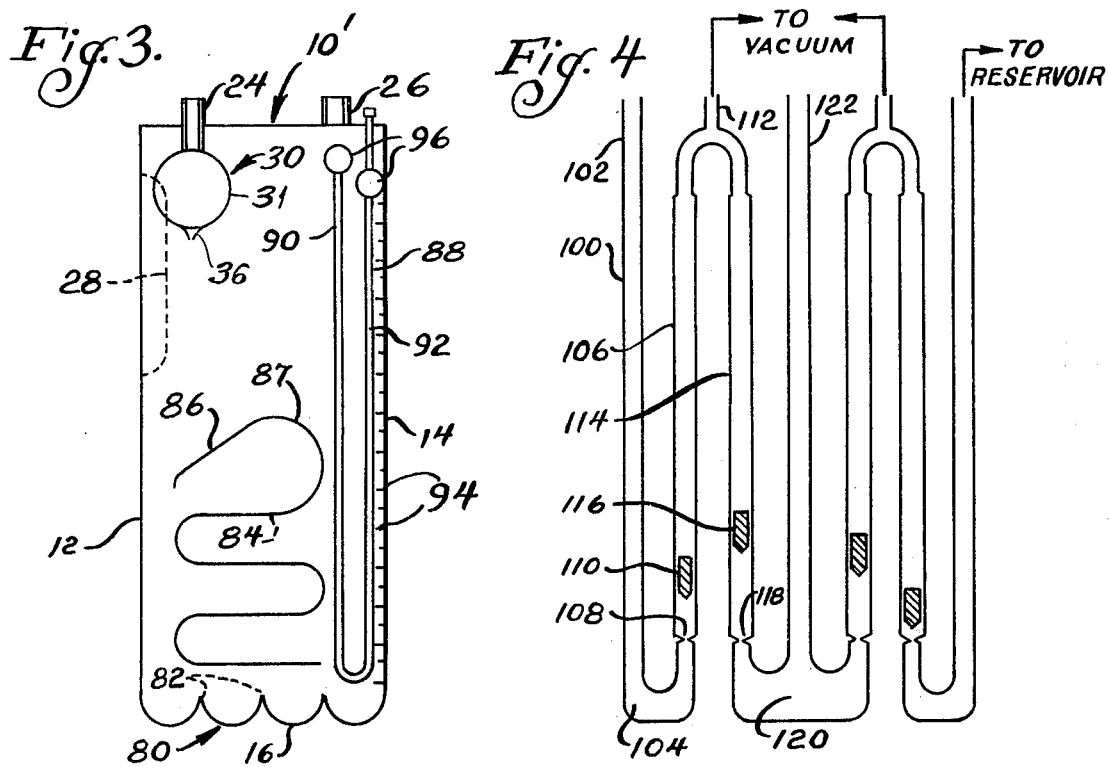

MEDICAL DRAINAGE DEVICE

BACKGROUND OF THE INVENTION

This invention relates to surgical suction systems, and more particularly, to a surgical suction system which may be driven in a variety of ways.

In the practice of surgery, there are several situations which require the creation of an evacuation mechanism within existing body spaces or spaces which potentially may be formed within the body. Evacuation is accomplished by means of insertion of a tube within the space, which tube is connected to a conduit system which in turn may be connected to any one of a variety of systems which create a mild vacuum or suction and include means for collecting the evacuated material in a reservoir.

The thoracic cavity is one body area which requires such an evacuation system following surgery of the chest. Another application for surgical suction systems exists in potential spaces under widely dissected skin flaps such as are developed following a radical mastectomy. Other situations requiring evacuation also exist. For example, various body secretions such as blood and plasma collect in spaces following surgery and occasionally, air may leak from a lung into the thoracic cavity following injury or surgery. Healing is promoted by the evacuation of blood or the air, as the case may be.

Present systems are driven by means of external vacuum pumps or remote suction sources as are typically available in most hospitals. Typically, the systems include various valving mechanisms such as a so-called "water seal" chamber or bottle. Typically, air will bubble through such a bottle or chamber, or to a trap to establish a desired vacuum level within the system. The continued bubbling is resonated by any container or chamber and is rather loud thereby being a source of bother and disturbance to a patient. Additionally, the prior art systems generally are keyed to but a single mode of operation. As a result, their lack of adaptability to varying situations frequently requires the presence of an attendant to perform specialized operations as, for example, hand milking the tube, thereby increasing the cost of use of such systems.

SUMMARY OF THE INVENTION

It is the principal object of the invention to provide a new and improved surgical suction system. More specifically, it is an object of the invention to provide such a system wherein the same may be driven by any of a variety of means to promote flexibility and eliminate absolute dependency on vacuum systems.

The exemplary embodiment of the invention achieves the foregoing object in a structure including an enlarged container having an inlet and an outlet. The container is formed of a resilient material of the type tending to restore itself to its original shape after distortion thereof such as any of a variety of plastics. Associated with the inlet is a check valve which is operative to substantially prevent backflow of fluid through the inlet. A check valve is also associated with the outlet so as to preclude backflow of fluid into the container through the outlet.

The container is provided with means formed in the walls thereof for facilitating compression of the same. Thus, by compressing the container to reduce the volume therein, fluid will be expelled through the outlet thereby establishing a partial vacuum within the container for drawing fluid from a patient into the container to be accumulated therein.

According to the preferred embodiment, the check valve associated with the inlet is actually within the container and includes a chamber having a compressible wall and terminating in a valve-like flap formation. When the container is compressed, the chamber of the valve will be slightly compressed so that the relatively small volume of fluid therein will be forced rearwardly through the inlet line to assist in agglomerating liquids or the like in a conduit connected to the inlet and to the patient.

The container also includes integral baffles therein of various configurations to assist in measuring fluid flowing into the container from a patient.

The check valve associated with the outlet may take on differing forms as desired. According to one embodiment of the invention, a U-shaped formation is employed with one leg thereof being connected to the outlet and the other leg being connected to atmosphere or to a source of regulated vacuum. Baffles are provided in each of the legs so that liquid in the base of the U cannot be forced out of the valve for sudden changes of pressure in the system.

Another embodiment of the invention employs rotameter-like floats in U tubes which also serve as check valve outlets.

The position of the floats within a leg of the system is taken as a measurement of the flow of fluid therethrough. Preferably, when this embodiment of a check valve associated with the outlet is employed, the container itself includes an integral manometer so that when the U tube is associated with a vacuum source, the vacuum may be regulated through adjustable constrictions in the vacuum line or the like and the precise degree of vacuum determined by reference to the manometer.

Other objects and advantages will become apparent from the following specification taken in conjunction with the accompanying drawings.

DESCRIPTION OF THE DRAWINGS

FIG. 1 is a perspective view of a container defining a reservoir made according to the invention;

FIG. 2 is a somewhat schematic elevational view of a check valve and vacuum regulating device;

FIG. 3 is a somewhat schematic elevation of a modified embodiment of the container; and FIG. 4 is a somewhat schematic, elevational view of a modified embodiment of a valve and flow measuring device.

DESCRIPTION OF THE PREFERRED EMBODIMENTS

One embodiment of a container or reservoir made according to the invention is illustrated in FIG. 1 and is generally designated 10. The container 10 is formed of a material that is resilient to the extent that once distorted from its original shape, it will return thereto. For purposes to be seen, it is also desirable that the container 10 be formed of a transparent material and to satisfy both of the foregoing requirements, it is preferred that the container 10 be formed of plastic.

The container 10 includes opposed end walls 12 and 14, a bottom wall 16, a top wall 18, and opposed side walls 20 and 22. The top wall includes an inlet tube 24 and an outlet tube 26, both of which are in fluid communication with the interior of the container 10. The upper ends of the side walls 12 and 14 are provided with accordion pleat-like formations 28 so that at least the upper portion of the container 10 can be collapsed by manual squeezing or mechanical compression.

When the upper portion of the container 10 is collapsed, as by squeezing in the manner aforesaid, the interior volume thereof is reduced. However, due to the aforementioned resilient characteristic of the material of which the container 10 is formed, it will tend to restore itself to the shape illustrated in FIG. 1.

Within the container 10 and in fluid communication with the inlet 12 is a balloon valve, generally designated 30, which acts as a check valve allowing fluid to enter the container 10 but precluding fluid in the container 10 from passing rearwardly through the inlet 24. The balloon valve 30 includes a bulbous chamber 31 which is in fluid communication with the inlet 24 by means of a tube 32. The bulbous chamber 31 is preferably formed of a flexible material such as plastic and normally will have an extremely thin wall such that when the container is partially collapsed, the resulting increase in pressure within the container will collapse the bulbous chamber 31.

The lower end of the bulbous chamber 31 includes a slightly elongated opening 34 through which fluid may pass from the inlet 24 to the interior of the container 10. Depending flaps 36, of which there are two arranged on opposite side of the opening 34, provide a valve-like formation which provide the above-mentioned check valve function. When the interior of the chamber 10 is at a lower pressure than that of the fluid to the inlet 24, such fluid may enter the chamber through the flaps 36. However, when the interior of the chamber 10 is at a greater pressure as, for example, when the upper end thereof is squeezed or compressed, such pressure will act against the exterior surfaces of the flaps to force the same together to seal against each other and at the same time collapse the bulbous chamber 31, as mentioned previously.

The inlet 24 is adapted to be connected by any suitable tubing to the cavity to be drained in a patient. As will be seen, when the pressure within the chamber 10 is established at a suitably low level, fluid, which may either be liquid or gaseous, will be drawn into the container 10. When the chamber interior pressure periodically is increased, as by compressing the upper end of the container, that amount of fluid within the bulbous chamber 31 will be directed rearwardly through the inlet 24 to the tube connecting the container 10 to the patient. In this respect, the volume of the bulbous chamber 31 is quite small compared to that of the container and is such that a relatively low volume of fluid will be backed up the tube connecting the container to the patient. As a result, a "milking" action is established in the tube to the patient which aids in the agglomeration of liquids or the like in the tube to replace the need for so-called "hand milking" required by the attending staff during the use of prior art systems.

Directly below the opening 34 in the balloon valve 30, a small compartment 40 is formed in the container 10. This is accomplished by the provision of diverging portions 42 in the side walls 20 and 22 and an upwardly extending baffle 44 interconnecting the side walls 20 and 22. The small compartment 40 will thus receive all liquid entering into the container 10, and by means of suitable gradations 46 on the side wall 20, the quantity of liquid being drained from the patient can be ascertained with relatively great accuracy. Where large volumes of liquid are being drained from the patient, the liquid will eventually spill over the top of the baffle 44 into the remainder of the container 10 and a relatively accurate measurement of such liquid accumulation can be ascertained through the use of gradations 48.

The outlet 26 is adapted to be connected to a check valve and/or a regulated source of vacuum. To this end, a combination valve and regulating apparatus is provided. The apparatus is illustrated in FIG. 2 and is adapted to accommodate two reservoirs so that a single regulating apparatus is sufficient for a two-bed hospital room.

With reference to FIG. 2, such an apparatus is illustrated. As is apparent, the same is symmetrical about its center line and, accordingly, only the left side thereof will be described. The same includes a U-shaped passage, generally designated 50, having a first leg 52, the upper end of which may be connected by tubing to the outlet 26. The opposite leg 54 is in fluid communication with a port 56 which, depending upon the mode of operation, may be connected to a vacuum source or open to atmosphere. A partition, schematically illustrated 57, separates the legs 52 and 54 and terminates at 58 short of the bottom wall 60 of the apparatus. In the area of the end 58 is an enlarged chamber 62 which may be provided with a volume of water sufficient to achieve a level above the end 58 to establish a so-called "water seal" for the conventional purpose known in the art. The water seal will, of course, serve as a check valve, permitting the egress of fluid from the outlet 26 while preventing free ingress into the chamber 10 through the outlet 26. The enlarged chamber 62 is preferably dome-shaped so that a small surface area of water is exposed to minimize evaporization and, furthermore, the volume provided is sufficient so that the presence of the water seal is assured for a prolonged period of time.

Near their upper ends, both of the legs 52 and 54 include bulbous formations 64 and 66 within which are disposed baffles 68. The bulbous formation 66 is open as at 70 to provide fluid communication to the port 56 and the baffles 68 perform the function of precluding the outflow of the water located within the chamber 62 in the event of abrupt pressure changes in the system as, for example, when the apparatus is being employed for draining the thoracic cavity and the patient coughs.

The apparatus also includes an interior chamber 72 in fluid communication with the opening 70 and the port 56. The chamber 72 is purposely enlarged to provide adequate volume for the water placed therein so that the apparatus may be used for a prolonged period of time without providing additional water. Water may be added to the respective chambers 62 and 72 quite easily through the ports 52 and 56.

The apparatus also includes a tube 74 which extends downwardly into the chamber 72 and has an open end 76 exposed to atmosphere. Indicia in the form of gradations 76 are located on the exterior wall of the apparatus adjacent the tube 74. As will be readily appreciated by those skilled in the art, when the chamber 72 is filled to a predetermined degree with water, and the port 56 is connected to a source of vacuum, the level of water in the chamber 72 acts to regulate the vacuum applied to the system.

As a result of the foregoing, it will be appreciated that through the use of the embodiments of the invention illustrated in FIGS. 1 and 2, the system may be driven either by connection to a conventional vacuum source or by periodic compression of the container 10. Such compression can be accomplished manually by squeezing the container or, if desired, a mechanical actuator could be employed for that purpose. For example, any mechanical or electromechanical apparatus having a reciprocal output can be arranged with respect to the container 10 so as to periodically cause compression of the upper portion thereof.

Turning now to FIG. 3, a modified embodiment of a container made according to the invention is illustrated. Where appropriate, reference numerals corresponding to those employed in the description of the embodiment in FIG. 1 are employed.

The embodiment illustrated in FIG. 3 includes a container, generally designated 10′, which is provided with an inlet 24 and associated balloon valve 30, as described previously. The same also includes an outlet 26 and opposed side walls 12 and 14. In the case of the embodiment illustrated in FIG. 3, only the side wall 12 is provided with a pleated formation 28.

The bottom 16 of the embodiment illustrated in FIG. 3, includes a scalloped formation, generally designated 80. Inwardly directed peaks 82 within the container provide the same function as the baffle 44. That is, the peaks 82 of the scalloped formation 80 define a plurality of small compartments, the first of which is directly below the balloon valve 30 and which receives liquids entering the same. The compartments will fill serially, providing an indication of the amount and rate of flow of liquids being drained from the patient.

The interior of the container 10′ includes a serpentine seal 84, the upper end 86 of which is slanted to act as a deflector for liquids entering through the balloon valve 30 to insure that it passes to the leftmost one of the small compartments defined by the peaks 82. As the container fills, the various steps in the serpentine seal 84 provide an indication of the amount of liquid being received in the container. To avoid the presence of an air lock, an opening 87 is provided in the uppermost flute of the seal 84.

The container 10′ is also provided with a U-tube manometer 88. One of the legs 90 thereof is in fluid communication with the interior of the container, while the other leg 92 is in effective fluid communication with the surrounding atmosphere. For vacuum measuring purposes, any suitable liquid may be placed within the manometer 88 and the difference in levels in the two legs 90 and 92 judged by indicia in the form of gradations 94.

To preclude loss of liquid in the U-tube manometer 88 during abrupt changes in pressure within the vessel as, again, when the same is being employed in draining a thoracic cavity and the patient coughs, the openings of both of the legs 90 and 92 are covered with domes 96 of a soft, resilient, but liquid impervious material. The use of such material in a dome form permits accurate readings to be obtained on the manometer 88 while serving as a barrier to liquid expulsion during such abrupt pressure changes.

With reference now to FIG. 4, an apparatus providing a valving function for use in connection with the outlet 26 of the container 10′ and for providing an indication of the rate of fluid flow from the cavity being drained is illustrated. Like the apparatus illustrated in FIG. 2, that shown in FIG. 4 is symmetrical about its center line and accordingly, only the left side will be described. A generally vertically arranged tube 100 is provided and the upper end 102 thereof is adapted to be connected as by tubing to the outlet 26. The lower end includes an enlarged chamber 104 which is connected to a second upwardly extending tube 106. Near the lowermost end of the tube 106 is a valve seat 108 and within the tube 106 is a float 110 which, when seated against the valve seat 108, precludes fluid from flowing from the tube 100 to the outlet 26.

The tube 106 includes a slightly increasing cross section from the bottom to top in the same manner as a conventional rotameter. As a result, the position of the float 10 within the tube 106 is a measure of the volumetric flow rate of fluid from the patient through the tube 106 when the upper end thereof is connected via an outlet 112 to a source of vacuum.

The outlet 112 is also connected to a tube 114 tapered in the same fashion as the tube 106 and also containing a float 116 and a valve seat 118. The lower end of the tube 114 is connected via an enlarged chamber 120 to an upwardly extending tube 122 which is open at its upper end to atmosphere. Thus, the position of the float 116 within the tube 114 provides an indication of the rate of inflow of air through the tube 122 to the system when the outlet 112 is connected to a source of vacuum.

The purpose of the enlarged chambers 104 and 120 is to accommodate compensation without establishing a seal within the system.

The apparatus illustrated in FIG. 4 is ideally suited for use with the container 10′ shown in FIG. 3 by connecting the upper end 102 of the tube 100 to the outlet 26 with or without connection of the outlet 112 to vacuum. Without connection of the outlet 112 to vacuum, the container 10′ and the suction system in which it is employed may be driven through periodic compression of the upper portion of the container 10′. In such a case, the float 110 serves as a check valve in fluid communication with the outlet 26.

When the outlet 112 is connected to a vacuum source, the flow rate to the source of vacuum may be suitably regulated by a clamp applied across a tube connecting the outlet 112 to the vacuum line and any desired vacuum established by monitoring the vacuum within the container 10′ through the use of the U-tube manometer 88. This system has the particular advantage that volumetric flow rate of fluids being withdrawn from the patient can be observed by observing the position of the floats 110 and 116.

From the foregoing, it will be appreciated that a surgical suction system made according to the invention readily accomplishes the highly desired functions of permitting flexibility of drive methods, eliminating noise attendant the use of prior art systems, etc. The same is susceptible to formation of plastic through the use of blow molding techniques or the like so that the components thereof are readily disposable after but a single use.

I claim:

1. A surgical suction device comprising: an enlarged container having an inlet for fluids and and outlet for fluids, said container being formed of a resilient material of a type tending to restore itself to an original shape following a distortion thereof from said original shape, said inlet being adapted to be connected to apparatus for insertion into an area of a patient to be drained; a check valve associated with said inlet for allowing fluid to pass into said container through said inlet while precluding substantial backflow of fluid from said container through said inlet; and means formed in at least a portion of said container facilitating compression of the same to reduce the volume therein said check valve associated with said inlet being located interiorly of said container and including a chamber formed of compressible material in fluid communication with said inlet and having a valve establishing fluid communication between the interior of said chamber and the interior of said container, said chamber having a relatively small volume compared to the volume of said container whereby compression of said container will cause partial collapse of said chamber to drive fluid contained therein backwardly through said inlet to provide a milking action assisting fluid in a conduit connected to said inlet to migrate to said container.

2. The surgical suction device of claim 1 wherein said container is generally rectangular in cross section and wherein said means for facilitating compression of said container comprise pleated formations in opposed side walls thereof.

3. The surgical suction device of claim 1 wherein said check valve establishing fluid communication between said chamber and said container comprises a pair of flaps on opposite sides of an opening between said container and said chamber and adapted to close said opening.

4. A surgical suction device comprising: an enlarged container having an inlet and an outlet, said container being formed of a resilient material of a type tending to restore itself to an original shape following a distortion thereof from said original shape, said inlet being adapted to be connected to apparatus for insertion into an area of a patient to be drained, said outlet being connected to check valve means permitting fluid to be exhausted from said container while preventing backflow of fluid into said container through said outlet in excess of a predetermined amount; a check valve associated with said inlet for allowing fluid to pass into said container through said inlet while precluding substantial backflow of fluid from said container through said inlet; and means formed in at least a portion of said container facilitating compression of the same to reduce the volume therein so that a predetermined vacuum may be established within said container; a baffle in said container and extending upwardly from the bottom wall thereof at a location subjacent said inlet to divide said container into a small compartment and a large compartment with the small compartment being subjacent said inlet to receive fluid entering said chamber therethrough; and indicia means on said container adjacent said small compartment whereby the volume of fluid entering said container and received in said small compartment can be determined.

5. The surgical suction device of claim 4 wherein said baffle is one of a series of inwardly directed projections in said container bottom wall provided by a scalloped formation thereof.

6. A surgical suction device comprising: an enlarged container having an inlet and an outlet, said container being formed of a resilient material of a type tending to restore itself to an original shape following a distortion thereof from said original shape, said inlet being adapted to be connected to apparatus for insertion into an area of a patient to be drained, said outlet being connected to check valve means permitting fluid to be exhausted from said container while preventing backflow of fluid into said container through said outlet in excess of a predetermined amount; a check valve associated with said inlet for allowing fluid to pass into said container through said inlet while precluding substantial backflow of fluid from said container through said inlet; and means formed in at least a portion of said container facilitating compression of the same to reduce the volume therein so that a predetermined vacuum may be established within said container; a U-tube manometer integral with said container and having one leg thereof opening interiorly of said container and another leg thereof opening exteriorly of said container, at least said one leg being covered with a dome of a flexible, soft material to preclude liquid within said manometer from being expelled therefrom during sudden pressure changes within the container of short duration.

7. A surgical suction system including a surgical suction device having an enlarged container having an inlet and an outlet, said container being formed of a resilient material of a type tending to restore itself to an original shape following a distortion thereof from said original shape, said inlet being adapted to be connected to apparatus for insertion into an area of a patient to be drained, said outlet being connected to check valve means permitting fluid to be exhausted from said container while preventing backflow of fluid into said container through said outlet in excess of a predetermined amount; a check valve associated with said inlet for allowing fluid to pass into said container through said inlet while precluding substantial backflow of fluid from said container through said inlet; and means formed in at least a portion of said container facilitating compression of the same to reduce the volume therein so that a predetermined vacuum may be established within said container; and means in fluid communication with said check valve means connected to said outlet adapted to be connected to a source of vacuum for regulating the vacuum within said container.

8. A surgical suction system according to claim 7 wherein said check valve means includes a U-shaped passage having one leg thereof connected to said outlet and the other leg thereof connected to said vacuum regulating means, and further including a baffle disposed in said one leg and adapted to block the flow of liquid material in said other leg toward said vacuum regulating means during abrupt changes in pressure in said system.

9. The surgical suction system of claim 8 wherein said one leg includes a bulbous chamber and said baffle is located in said bulbous chamber.

10. The surgical suction system of claim 9 wherein both said legs include said bulbous chamber with baffles therein.

* * * * *